United States Patent
Auvin et al.

(10) Patent No.: US 6,821,986 B2
(45) Date of Patent: Nov. 23, 2004

(54) AMINO ACID DERIVATIVES AND THEIR USE AS MEDICINES

(75) Inventors: Serge Auvin, Mauchamps (FR); Jeremiah Harnett, Gif-sur-Yvette (FR); Pierre-Etienne Chabrier de Lassauniere, Paris (FR)

(73) Assignee: Societe de Conseils de Recherchet et E'Applications Scientifiques (S.C.R.A.S.) (FR)

( * ) Notice: Subject to any disclaimer, the term of this patent is extended or adjusted under 35 U.S.C. 154(b) by 62 days.

(21) Appl. No.: 10/275,057

(22) PCT Filed: May 4, 2001

(86) PCT No.: PCT/FR01/01358
§ 371 (c)(1),
(2), (4) Date: Oct. 31, 2002

(87) PCT Pub. No.: WO01/85677
PCT Pub. Date: Nov. 15, 2001

(65) Prior Publication Data
US 2003/0166630 A1 Sep. 4, 2003

(30) Foreign Application Priority Data

May 5, 2000 (FR) .............................. 00 05758
Sep. 1, 2000 (FR) .............................. 00 11168

(51) Int. Cl.$^7$ .................. C07D 209/14; A61K 31/404; A61P 25/16; A61P 9/10
(52) U.S. Cl. ................. 514/311; 548/465; 548/494; 548/495; 548/496; 546/166; 514/419
(58) Field of Search ................. 548/465, 494, 548/495, 496; 546/166; 514/311, 419

(56) References Cited

U.S. PATENT DOCUMENTS

| 4,564,695 A | 1/1986 | Kuroiwa et al. ............... 560/13 |
| 5,059,712 A | 10/1991 | Griffith ....................... 562/560 |
| 5,468,476 A | 11/1995 | Ahluwalia et al. ............ 424/73 |
| 5,972,940 A | 10/1999 | Broquet et al. .......... 514/238.5 |

OTHER PUBLICATIONS

Dagan et al, "tuftsin . . . Bioactivity", Journal of Medical Chemistry, vol. 29, No. 10, 1986, pp. 1961–1968.
Medhurst et al, "N$^G$–nitro–. . . Tissues", Chemical Abstracts, vol. 123, No. 11, 1995, p. 124.

*Primary Examiner*—Richard L Raymon
*Assistant Examiner*—Kahsay Habte
(74) *Attorney, Agent, or Firm*—Muserlian, Lucas and Mercanti

(57) ABSTRACT

Novel compounds of formula $$A-X-N(R^1)-CH(V-NH-C(D)=NH)-C(=O)-W-Y-A' \quad (I)$$

wherein the substituents are defined as in the specification and are useful for inhibiting neuronal NO synthase or inducible NO synthase as well as inhibiting lipidic peroxidation.

11 Claims, No Drawings

AMINO ACID DERIVATIVES AND THEIR USE AS MEDICINES

This application is a 371 of PCT/FR01/01358 filed May 4, 2001.

The present invention relates to new derivatives of amino acids and their use as medicaments. These derivatives have an inhibitory activity on NO-synthase enzymes producing nitrogen monoxide NO and/or (according to preference):

either an activity which traps the reactive oxygen species (ROS);

or an antioxidant regenerating activity such as glutathione or reactive oxygen species (ROS) traps and more generally an influence on the redox status of the thiol groups.

Therefore the invention relates in particular to the derivatives corresponding to general formula (I) defined hereafter, their preparation methods, the pharmaceutical preparations containing them and their use for therapeutic ends, in particular their use as inhibitors of NO-synthases and/or (according to preference):

either as ROS traps;

or as agents allowing the regeneration of antioxidants such as glutathione or ROS traps entities and intervening in a more general fashion in the redox status of the thiol groups.

Given the potential role of NO, the ROS's and the metabolism of glutathione in physiopathology, the new derivatives described corresponding to general formula (I) may produce beneficial or favourable effects in the treatment of pathologies where nitrogen monoxide, the ROS's and the metabolism of glutathione as well as the redox status of the thiol groups are involved, and in particular:

cardiovascular and cerebrovascular disorders comprising, for example, atherosclerosis, migraine, arterial hypertension, septic shock, cardiac or cerebral infractions of ischemic or haemorrhagic origin, ischemias and thromboses;

disorders of the central or peripheral nervous system such as, for example, neurodegenerative diseases where cerebral infarctions, sub-arachnoid haemorrhage, ageing, senile dementia, including Alzheimer's disease, Huntington's chorea, Parkinson's disease, Freidreich's ataxia, Creutzfeld-Jacob's disease and prion diseases, amyotrophic lateral sclerosis, but also pain, cerebral or bone marrow traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (anorexia, bulimia, etc.) can be mentioned in particular;

disorders of the skeletal muscle and of the neuromuscular junctions (myopathy, myositis) as well as skin diseases;

proliferative and inflammatory diseases such as, for example, atherosclerosis, pulmonary hypertension, respiratory distress, glomerulonephritis, cataracts, portal hypertension, psoriasis, arthrosis and rheumatoid arthritis, fibroses, amyloidoses, inflammations of the gastrointestinal system (colitis, Crohn's disease) or of the pulmonary system and airways (asthma, sinusitis, rhinitis) as well as contact or delayed hypersensitivities;

organ transplants;

auto-immune and viral diseases such as lupus, AIDS, parasitic and viral infections, diabetes and its complications including retinopathies, nephropathies and polyneuropathies, multiple sclerosis, myopathies;

cancer;

autosomal genetic diseases such as Unverricht-Lundborg disease;

neurological diseases associated with intoxications (Cadmium poisoning, inhalation of n-hexane, pesticides, herbicides), associated with treatments (radiotherapy) or disorders of genetic origin (Wilson's disease)

impotence linked with diabetes;

all the pathologies characterized by a production or a dysfunction of nitrogen monoxide and/or ROS or the metabolism of glutathione and of the redox status of thiol groups.

In all these pathologies, there is experimental evidence demonstrating the involvement of nitrogen monoxide or of a dysfunction of the metabolism of glutathione (Kerwin et al., Nitric oxide: a new paradigm for second messengers, *J. Med. Chem.* 38, 4343–4362, 1995; Packer et al., Alpha-lipoic acid as biological antioxidant, *Free Radical Biology & Medicine* 19, 227–250, 1995). In this context, medicaments which can inhibit the formation of nitrogen monoxide, trap the ROS's or re-establish the biological functionality of the thiol groups or glutathione can have beneficial effects.

Compounds comprising both inhibitory properties of the NO-synthases and ROS trapping properties have already been described by the Applicant in earlier patent applications (cf. PCT Applications WO 98/42696, WO 98/58934, WO 00/02860, WO 00/17190 and WO 00/17191). More recently derivatives of lipoic acid having both inhibitory properties of the NO-synthases and regenerating properties of antioxidants or of ROS traps and more generally have an influence on the redox status of thiol groups have also been described more recently in the PCT Application WO 00/59899

The compounds of the invention correspond to general formula (I)

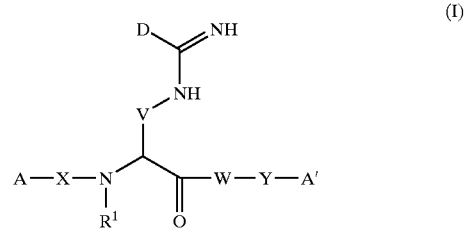

in which $R^1$ represents a hydrogen atom or an alkyl radical;

A and A' represent a hydrogen atom or one of the following radicals:

a

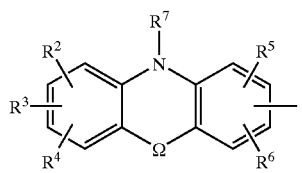

radical, in which $R^2$, $R^3$, $R^4$, $R^5$, $R^6$ represent, independently, a hydrogen atom, a halogen, the OH group, an alkyl, alkoxy, cyano, nitro or $NR^8R^9$ radical, $R^8$ and $R^9$ representing, independently, a hydrogen atom, an alkyl radical or a —$COR^{10}$ group, or $R^8$ and $R^9$ form together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^{10}$ representing a hydrogen atom, an alkyl, alkoxy or $NR^{11}R^{12}$ radical, $R^{11}$ and $R^{12}$ representing, independently, a hydrogen atom or an alkyl radical, or $R^{11}$ and $R^{12}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^7$ represents a hydrogen atom, an alkyl radical or a —$COR^{13}$ group, $R^{13}$ representing a hydrogen atom, an alkyl or alkoxy or $NR^{14}R^{15}$ radical, $R^{14}$ and $R^{15}$ representing independently, a hydrogen atom or an alkyl radical, or $R^{14}$ and $R^{15}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, and Ω does not exist, or represents a bond, O or S or also an $NR^{16}$ radical, in which $R^{16}$ represents a hydrogen atom or an alkyl radical;

or a

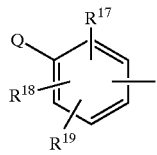

radical, in which $R^{17}$, $R^{18}$ and $R^{19}$ represent, independently, a hydrogen, a halogen, the OH or $SR^{20}$ group or an alkyl, alkenyl or alkoxy radical or an $NR^{21}R^{22}$ radical, $R^{20}$ representing a hydrogen atom or an alkyl radical, $R^{21}$ and $R^{22}$ representing, independently, a hydrogen atom, an alkyl radical or a —$COR^{23}$ group, or $R^{21}$ and $R^{22}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^{23}$ representing a hydrogen atom, an alkyl, alkoxy or $NR^{24}R^{25}$ radical, $R^{24}$ and $R^{25}$ representing, independently, a hydrogen atom or an alkyl radical, or $R^{24}$ and $R^{25}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, and Q represents —$OR^{26}$, —$SR^{26}$ or a phenyl radical substituted by one or more substituents chosen from a halogen, the OH group, an alkyl, alkoxy, cyano, nitro or $NR^8R^9$ radical, $R^{26}$ representing a hydrogen atom or an alkyl radical, $R^8$ and $R^9$ representing, independently, a hydrogen atom, an alkyl radical or a —$COR^{10}$ group, or $R^8$ and $R^9$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^{10}$ representing a hydrogen atom, an alkyl, alkoxy or $NR^{11}R^{12}$ radical, $R^{11}$ and $R^{12}$ representing, independently, a hydrogen atom or an alkyl radical, or $R^{11}$ and $R^{12}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, or a

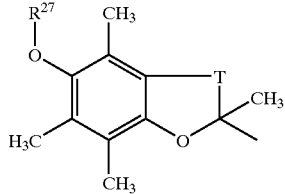

radical in which $R^{27}$ represents a hydrogen atom, an alkyl radical or an aralkyl radical, T representing a —$(CH_2)_m$— radical with m=1 or 2;

or a

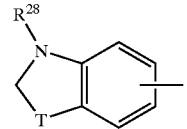

radical in which $R^{28}$ represents a hydrogen atom, an alkyl, aminoalkyl, alkylaminoalkyl, dialkylaminoalkyl or aralkyl radical the aryl group of which is optionally substituted by one or more substituents chosen independently from the OH group, a halogen atom, an alkyl, alkoxy, nitro or —$NR^{29}R^{30}$ radical, in which $R^{29}$ and $R^{30}$ represent, independently, a hydrogen atom, an alkyl radical or a —$COR^{31}$ group, or $R^{29}$ and $R^{30}$ form together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^{31}$ representing a hydrogen atom, an alkyl or alkoxy or $NR^{32}R^{33}$ radical, $R^{32}$ and $R^{33}$ representing, independently, a hydrogen atom or an alkyl radical, or $R^{32}$ and $R^{33}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, T representing a —(CH$_2$)$_m$— radical with m=1 or 2; or a

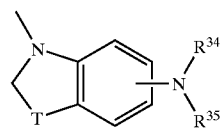

radical in which $R^{34}$ and $R^{35}$ represent independently a hydrogen atom or an alkyl or aralkyl radical the aryl group of which is optionally substituted by one or more substituents such as the OH group, the alkyl, halogen, nitro, alkoxy or —$NR^{36}R^{37}$ radicals, in which $R^{36}$ and $R^{37}$ represent, independently, a hydrogen atom, an alkyl radical or a —$COR^{38}$ group, or $R^{36}$ and $R^{37}$ form together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, $R^{38}$ representing a hydrogen atom, an alkyl or alkoxy or $NR^{39}R^{40}$ radical, $R^{39}$ and $R^{40}$ representing, independently, a hydrogen atom or an alkyl radical, or $R^{39}$ and $R^{40}$ forming together with the nitrogen atom an optionally substituted heterocycle containing 4 to 7 members and 1 to 3 heteroatoms including the nitrogen atom already present, the additional heteroatoms being chosen independently from the group constituted by the O, N and S atoms, said heterocycle being for example azetidine, pyrrolidine, piperidine, piperazine, morpholine or thiomorpholine, T representing a —(CH$_2$)$_m$— radical with m=1 or 2; or a

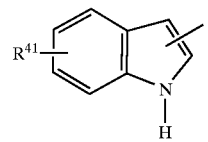

radical in which $R^{41}$ represents a hydrogen atom, the OH group, or an alkyl or alkoxy radical;

or finally a

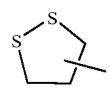

D represents a linear or branched alkyl radical having 1 to 6 carbon atoms, carbocyclic or heterocyclic aryl with 5 or 6 members containing 1 to 4 heteroatoms chosen from O, S and N (and in particular the thiophene, furane, pyrrole or thiazole radicals), the carbocyclic or heterocyclic aryl radical being optionally substituted by one or more groups chosen independently from the linear or branched alkyl, alkenyl or alkoxy radicals having 1 to 6 carbon atoms, or D represents an $NR^{42}R^{43}$ radical, in which $R^{42}$ and $R^{43}$ represent, independently, a hydrogen atom or a linear or branched alkyl, alkenyl or alkynyl radical having 1 to 6 carbon atoms or a cyano, nitro or amino radical, or $R^{42}$ and $R^{43}$ form together with the nitrogen atom a non-aromatic heterocycle with five to six members, the elements of the chain being chosen from a group comprising —CH$_2$—, —NH—, —O— or —S—;

or also D represents an —$SR^{44}$ radical, in which $R^{44}$ represents a linear or branched alkyl radical having 1 to 6 carbon atoms optionally substituted by a group chosen from: —OH, halogen, amino, cyano and aralkyl;

X represents a —(CH$_2$)$_n$—, —(CH$_2$)$_n$—CO—, —O—(CH$_2$)$_p$—, —S—(CH$_2$)$_p$—, —CH=CH—(CH$_2$)$_p$— or —CH=CH—(CH$_2$)$_n$—CO— radical, n being an integer from 0 to 6 and p being an integer from 1 to 6;

W represents —O— or —$NR^{45}$—, and $R^{45}$ representing a hydrogen atom or an alkyl radical;

Y represents a radical chosen from —(CH$_2$)$_t$—, —(CH$_2$)$_q$—O—, —(CH$_2$)$_q$—S— and —(CH$_2$)$_q$—$NR^{46}$— and $R^{46}$ representing a hydrogen atom or an alkyl radical, t being an integer from 0 to 6 and q being an integer from 2 to 6;

V represents a radical chosen from the —(CH$_2$)$_r$—, —(CH$_2$)$_r$—O—(CH$_2$)$_s$—, —(CH$_2$)$_r$—S—(CH$_2$)$_s$—, —(CH$_2$)$_r$—S(O)—(CH$_2$)$_s$— and —(CH$_2$)$_r$—S(O)$_2$—(CH$_2$)$_s$— radicals r being an integer from 1 to 6, s being an integer from 2 to 6;

it being understood that one of A and A' represents a hydrogen atom and the other does not represent a hydrogen atom;

or are salts of the compounds of general formula (I) as defined above.

These compounds have an inhibitory activity on the NO-synthase enzymes producing nitrogen monoxide NO and/or (according to preference):

either an activity which traps the reactive oxygen species (ROS) when neither A nor A' represents the

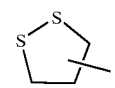

radical;

or a regenerative activity on antioxidants or entities which trap the reactive oxygen species (ROS) and more generally an influence on the redox status of the thiols group, in the particular case where one of A and A' represents the

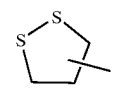

radical.

By alkyl, unless otherwise specified, is meant a linear or branched alkyl radical containing 1 to 12 carbon atoms, and preferably 1 to 6 carbon atoms. By alkenyl, unless otherwise specified, is meant a linear or branched alkyl radical containing 1 to 6 carbon atoms and having at least one unsaturation (double bond). By alkynyl, unless otherwise specified, is meant a linear or branched alkyl radical containing 1 to 6 carbon atoms and having at least one double unsaturation (triple bond). By carbocyclic or heterocyclic aryl, is meant a carbocyclic or heterocyclic system comprising at least one aromatic ring, a system being referred to as heterocyclic when at least one of the rings which compose it contains a heteroatom (O, N or S). By haloalkyl, is meant an alkyl radical of which at least one of the hydrogen atoms (and optionally all) is replaced by a halogen atom.

By alkylthio, alkoxy, haloalkyl, haloalkoxy, aminoalkyl, alkenyl, alkynyl, aralkyl radicals, is meant respectively the alkylthio, alkoxy, haloalkyl, haloalkoxy, aminoalkyl, alkenyl, alkynyl, aralkyl radicals the alkyl radical of which has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen is meant the fluorine, chlorine, bromine or iodine atoms.

In certain cases, the compounds according to the present invention can contain asymmetrical carbon atoms. As a result, the compounds according to the present invention have two possible enantiomeric forms, i.e. the "R" and "S" configurations. The present invention includes the two enantiomeric forms and all combinations of these forms, including the racemic "RS" mixtures. In a effort to simplify matters, when no specific configuration is indicated in the structural formulae, it should be understood that the two enantiomeric forms and their mixtures are represented.

In the general formula (I), when A or A' represents the

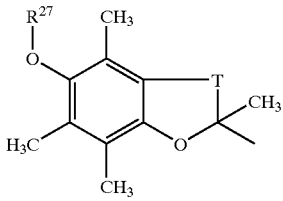

radical, $R^{27}$ will preferably represent a hydrogen atom or an alkyl radical and T will preferably represent the —$(CH_2)_2$— radical.

Furthermore, when A or A' represents the

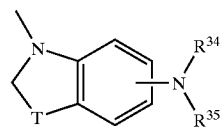

radical, $R^{34}$ and $R^{35}$ will preferably represent radicals selected independently from a hydrogen atom and an alkyl radical and T will preferably represent the —$(CH_2)$— radical.

Also preferably, the compounds of general formula (I) according to the invention will include at least one of the following characteristics:

an A or A' group representing one of the following radicals:
either the

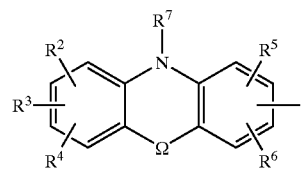

radical in which $R^2$, $R^3$, $R^4$, $R^5$, $R^6$ represent, independently, a hydrogen atom or an alkyl or alkoxy radical, $R^7$ represents a hydrogen atom and Ω does not exist or represents a bond or S;
or the

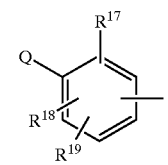

radical in which Q represents —$OR^{26}$ or —$SR^{26}$ and $R^{17}$, $R^{18}$ and $R^{19}$ represent independently a hydrogen atom, the OH, $SR^{20}$ or $NR^{21}R^{22}$ group or an alkyl or alkoxy radical, $R^{26}$ representing a hydrogen atom or an alkyl radical, $R^{20}$ representing a hydrogen atom or an alkyl radical, and $R^{21}$ and $R^{22}$ representing, independently, a hydrogen atom or an alkyl radical;
or the

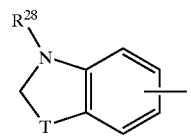

radical in which $R^{28}$ represents a hydrogen atom or an alkyl, aminoalkyl, alkylaminoalkyl, dialkylaminoalkyl or aralkyl radical the aryl group of which is optionally substituted by one or more radicals chosen independently from an alkyl radical and the —$NR^{29}R^{30}$ radical in which $R^{29}$ and $R^{30}$ represent, independently, a hydrogen atom or an alkyl radical, T representing a —$(CH_2)_m$— radical with m=1 or 2;
or finally the

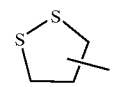

radical;

D representing a carbocyclic or heterocyclic aryl radical with 5 or 6 members containing 1 to 4 heteroatoms chosen from O, S and N, the carbocyclic or heterocyclic aryl radical being optionally substituted by one or more groups chosen independently from the linear or branched alkyl, alkenyl or alkoxy radicals having 1 to 6 carbon atoms, or also D representing an $NR^{42}R^{43}$ radical, in which $R^{42}$ and $R^{43}$ represent, independently, a hydrogen atom or a linear or branched alkyl, alkenyl or alkynyl radical having 1 to 6 carbon atoms or a cyano, nitro or amino radical, or $R^{42}$ and $R^{43}$ form together with the nitrogen atom a non-aromatic heterocycle with five to six members, the elements of the chain being chosen from a group comprising —$CH_2$—, —NH—, —O— or —S—;

V representing a —$(CH_2)_r$—, —$(CH_2)_r$—O—$(CH_2)_s$— or —$(CH_2)_r$—S—$(CH_2)_s$— radical, r being an integer from 1 to 6 and s an integer from 2 to 6;

W representing —O— or —NH—;

X representing a —$(CH_2)_n$—, —$(CH_2)_n$—CO—, —O—$(CH_2)_p$— or —S—$(CH_2)_p$— radical, n being an integer from 0 to 6 and p an integer from 1 to 6;

Y representing a radical chosen from —$(CH_2)_t$—, —$(CH_2)_q$—O— and —$(CH_2)_q$—$NR^{46}$—, $R^{46}$ representing a hydrogen atom or an alkyl radical, t representing an integer from 0 to 6 and q an integer from 2 to 6.

More preferentially, the compounds of general formula (I) according to the invention will include at least one of the following characteristics:

an A or A' group representing one of the following radicals:
either the

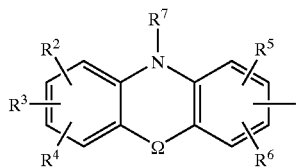

radical in which $R^2$, $R^3$, $R^4$, $R^5$, $R^6$ represent, independently, a hydrogen atom or an alkyl or alkoxy radical, $R^7$ represents a hydrogen atom and Ω does not exist or represents a bond or S;
or the

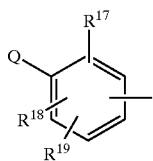

radical in which Ω represents OH and $R^{17}$, $R^{18}$ and $R^{19}$ represent independently a hydrogen atom, the OH, $SR^{20}$ or $NR^{21}R^{22}$ group or an alkyl radical or alkoxy,
$R^{20}$ representing an alkyl radical,
$R^{21}$ and $R^{22}$ representing, independently, a hydrogen atom or an alkyl radical;
or the

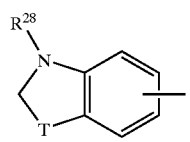

radical in which $R^{28}$ represent an alkyl, aminoalkyl, alkylaminoalkyl, dialkylaminoalkyl or aralkyl radical;
or finally the

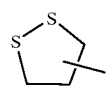

radical;

D representing a heterocyclic aryl radical with 5 members containing 1 to 4 heteroatoms chosen from O, S and N, or also D representing an $NR^{42}R^{43}$ radical, in which $R^{42}$ and $R^{43}$ represent, independently, a hydrogen atom or a linear or branched alkyl radical having 1 to 6 carbon atoms or a nitro radical, or $R^{42}$ and $R^{43}$ form together with the nitrogen atom a non-aromatic heterocycle with five to six members, the elements of the chain being chosen from a group comprising —$CH_2$—, —NH—, —O— or —S—;

V representing a —$(CH_2)_r$— radical, r being an integer from 1 to 6;

W representing —NH—;

X representing a —$(CH_2)_n$— or —$(CH_2)_n$—CO— radical, n being an integer from 0 to 6;

Y representing a radical chosen from —$(CH_2)_t$—, —$(CH_2)_q$—O— and —$(CH_2)_q$—NH—, t representing an integer from 0 to 6 and q an integer from 2 to 6.

Yet more preferentially, the compounds of general formula (I) according to the invention will include at least one of the following characteristics:

an A or A' group representing one of the following radicals:
either the

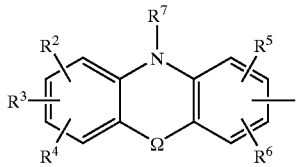

radical in which $R^2$, $R^3$, $R^4$, $R^5$, $R^6$ represent, independently, a hydrogen atom or an alkyl or alkoxy radical, $R^7$ represents a hydrogen atom and Ω does not exist or represents a bond or S;
or the

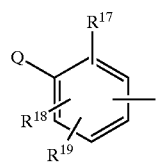

radical in which Q represents OH and two of $R^{17}$, $R^{18}$ and $R^{19}$ represent alkyl radicals, the third being chosen from a hydrogen atom and an alkyl, alkoxy or alkylthio radical;
or the

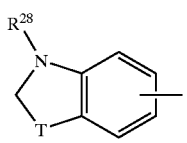

radical in which $R^{28}$ represents an alkyl, aminoalkyl, alkylaminoalkyl or dialkylaminoalkyl radical; or finally the

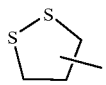

radical;

D representing the —NH—NO$_2$. radical

V representing a —(CH$_2$)$_r$— radical, r being an integer from 1 to 5 and preferably an integer from 2 to 4;

Y representing a —(CH$_2$)$_t$— radical, t representing an integer from 0 to 6.

In particular, a subject of the invention is the following compounds described in the examples:

- -(2S)-2-amino-N-(4-anilinophenyl)-5-{[imino(2-oxido-2-oxohydrazino)methyl]amino}pentanamide;
- -(2S)-2-amino-5-{[imino(2-oxido-2-oxohydrazino)methyl]amino}-N-(1-methyl-2,3-dihydro-1H-indol-5-yl)pentanamide;
- -(2S)-2-[(3,5-ditert-butyl-4-hydroxybenzyl)amino]-5-{[imino(2-oxido-2-oxohydrazino)methyl]amino}pentanoic acid;
- -methyl (2S)-2-{[5-(1,2-dithiolan-3-yl)pentanoyl]amino}-5-{[imino(2-oxido-2-oxohydrazino)methyl]amino}pentanoate;
- -(2S)-2-{[5-(1,2-dithiolan-3-yl)pentanoyl]amino}-5-{[imino(2-oxido-2-oxohydrazino)methyl]amino}pentanoic acid;

as well as their salts.

A subject of the invention is also, as medicaments, the compounds of general formula (I) described previously or their pharmaceutically acceptable salts. It also relates to pharmaceutical compositions containing these compounds or their pharmaceutically acceptable salts, with one or more pharmaceutically acceptable excipients. It also relates to the use of these compounds or of their pharmaceutically acceptable salts to produce the medicaments intended:

1) to inhibit neuronal NO synthase or inductible NO synthase; to inhibit lipidic peroxidation; or finally to provide the dual function of inhibition of NO synthase and inhibition of lipidic peroxidation, when neither A nor A' represents the

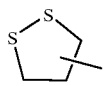

radical;

2) to inhibit neuronal NO synthase or inductible NO synthase; to regenerate antioxidants or ROS trapping entities and more generally to intervene in the redox status of the thiols group; or finally to provide the dual function of inhibition of NO synthase and regeneration of antioxidants or entities which trap ROS and more generally to intervene in the redox status of the thiols group, when the one of A and A' represents the

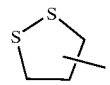

radical.

Preferably, the compounds of general formula (I) as previously defined or the pharmaceutically acceptable salts of such compounds will be used for preparing a medicament intended to treat cardiovascular and cerebrovascular disorders or central or peripheral nervous system disorders.

By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, pamoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201–217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

Administration of a medicament according to the invention can be carried out by topical, oral, parenteral route, by intramuscular injection, etc.

The administration dose envisaged for a medicament according to the invention is comprised between 0.1 mg and 10 g depending on the type of active compound used.

According to the invention, the compounds of general formula (I) can be prepared using the processes described hereafter.

Preparation of the Compounds of General Formula (I)

The compounds of general formula (I) can be prepared according to different synthesis strategies which are described in the following diagrams:

Diagram 1

A)

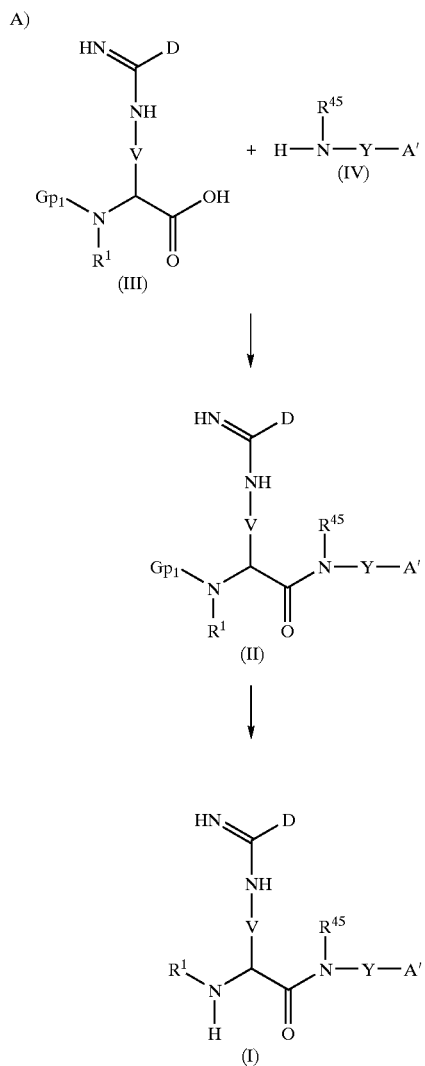

The aminocarboxamides of general formula (I), Diagram 1, in which A', D, V, Y and $R^1$ are as defined above with, in particular, A representing a hydrogen atom, X a (—$(CH_2)_n$— bond with n=0) and W=—$NR^{45}$— are prepared in two stages, from the protected amino acids ($Gp_1$ being a protective group of carbamate type) of general formula (III) and the amines of general formula (IV). Their condensation is carried out under standard conditions for peptide synthesis (M. Bodanszky and A. Bodanszky, The Practice of Peptide Synthesis, 145 (Springer-Verlag, 1984)) in THF, dichloromethane, pyridine or DMF in the presence of a coupling reagent such as dicyclohexylcarbodiimide (DCC), 1,1'-carbonyldiimidazole (CDI) (J. Med. Chem. (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)) in order to produce the carboxamides of general formula (II). Cleavage of the protective group $Gp_1$ is then carried out in a standard fashion, for example in the presence of a strong acid, of a secondary amine or under conditions of hydrogenolysis, according to methods described in the literature (T. W. Greene and P. G. M. Wuts, Protective Groups in Organic Synthesis, Second edition (Wiley-Interscience, 1991)), in order to produce the final compounds of general formula (I). The syntheses of the non-commercial compounds of general formula (III) and (IV) are described below.

B) Alternatively the derivatives of amino acids of general formula (I) can be prepared according to the strategy described in Diagram 2, in which A, D, V and $R^1$ are as defined above with A' representing a hydrogen atom, W=—O—, Y=—$(CH_2)_t$— (t=0), X=—$(CH_2)_n$—, —O—$(CH_2)_p$—, —S—$(CH_2)_p$— or —CH=CH— $(CH_2)_p$—(n being in this case an integer from 1 to 6) and $Gp_2$ being an alkyl or arylalkyl group.

Diagram 2

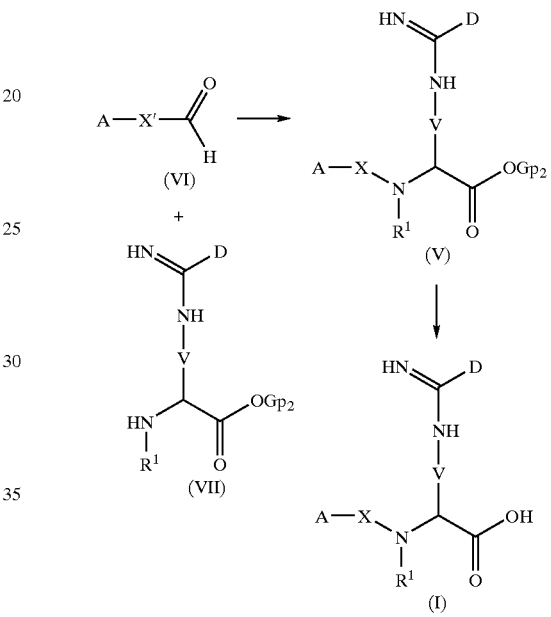

The derivatives of aminoesters of general formula (V) are accessible, during a reducing amination stage, by condensation of the aldehydes of general formula (VI) and of the α-aminoesters of general formula (VII). This condensation is carried out in a standard fashion at 20° C. in an alcoholic solvent such as methanol in the presence of a dehydration agent, such as molecular sieves, and of a reducing agent such as, for example, $NaBH_3CN$. This stage leads to the monoalkylation product of general formula (V). Deprotection of the acid function is then carried out in a standard fashion according to the nature of $Gp_2$, for example, by saponification using LiOH or according to methods described in the literature (T. W. Greene and P. G. M. Wuts, Protective Groups in Organic Synthesis, Second edition (Wiley-Interscience, 1991)), in order to produce the amino acids of general formula (I). The syntheses of the non-commercial compounds of general formula (VI) and (VII) are described below.

C) Moreover, the carboxamides of general formula (I) can also be prepared according to the strategy described in Diagram 3, in which A, D, V and $R^1$ are as defined above with A' representing a hydrogen atom, W=—O—, Y=—$(CH_2)_t$— (t=0), X=—$(CH_2)_n$—CO— or —CH=CH—$(CH_2)_n$—CO— (n being an integer from 0 to 6) and $GP_2$ being an alkyl or arylalkyl group.

Diagram 3

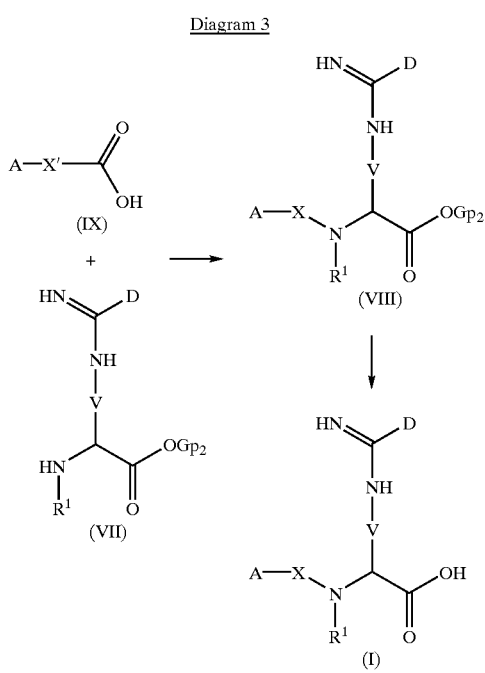

Condensation of the carboxylic acids of general formula (IX) with the α-aminoesters of general formula (VII) is carried out under standard conditions for peptide synthesis as previously described. The carboxamide ester of general formula (VIII) obtained intermediately is then deprotected according to a protocol described in Diagram 2 in order to produce the carboxamide acids of general formula (I). The syntheses of the non-commercial compounds of general formula (IX) are described below.

Preparation of the Intermediates of General Formula (III)

The compounds of general formula (III) can be prepared from the intermediates of general formula (III.2) according to Diagram 1.1 where D, V and $R^1$ are as defined above, $Gp_1$ being a protective group of carbamate type and $Gp_2$ is an alkyl or arylalkyl group.

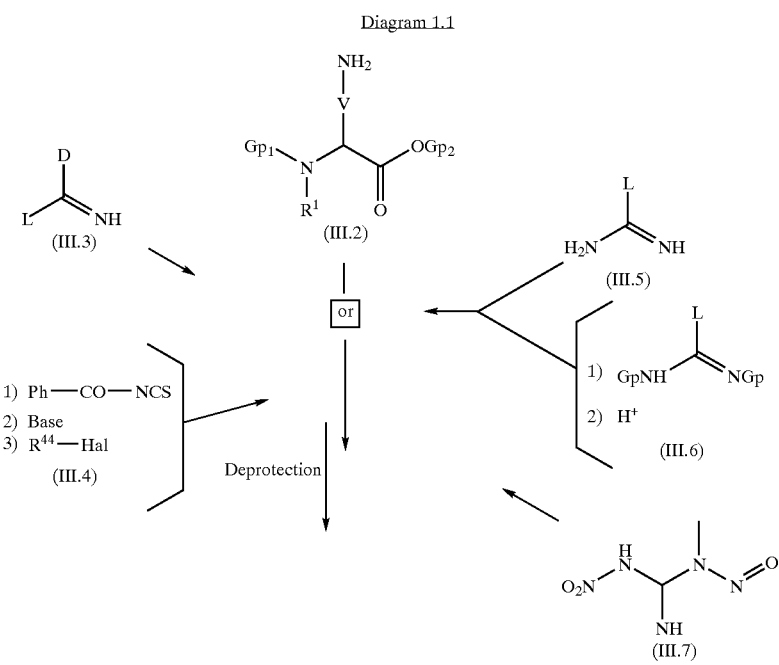

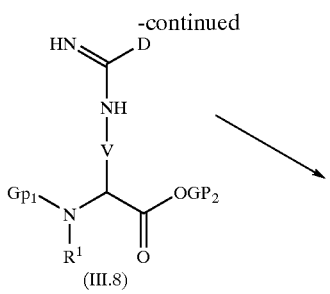

(III.8)

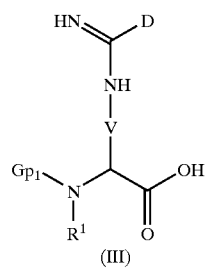

(III)

The amines of general formula (III.2) can be condensed with compounds of general formula (III.3), in which L represents a parting group (an alkoxy, alkylthio, aralkylthio, sulphonic acid, halide, aryl alcohol or tosyl radical), by heating in an alcohol (for example in methanol or isopropanol), optionally in the presence of DMF, at a temperature comprised between 20 and 100° C. for a duration generally comprised between a few hours and overnight, in order to produce the intermediates of general formula (III.8).

In the case where D is an amine, the intermediates of general formula (III) are guanidines. These can be prepared, for example, by the condensation of the amines of general formula (III.2) with the derivatives of general formula (III.5) or (III.6). The reagents of general formula (III.5) in which L represents, for example, a pyrazole ring are condensed with the amines of general formula (III.2) according to the conditions described in the literature (*J. Org. Chem.* (1992) 57, 2497–2502) similarly for the reagents of general formula (III.6) in which L represents, for example, a pyrazole ring and Gp represents the Boc group (*Tetrahedron Lett.* (1993) 34 (21), 3389–3392) or when L represents the —N—SO$_2$—CF$_3$ group and Gp represents the Boc group (*J. Org. Chem.* (1998) 63, 3804–3805). The deprotection of the guanidine function can then be carried out, for example, in the presence of a strong acid such as for example trifluoroacetic acid in order to produce the intermediates of general formula (III.8).

In the case where D=—NHNO$_2$, the intermediates of general formula (III.8) can be prepared, for example, by the condensation of the amines of general formula (III.2) with the reagent of general formula (III.7) (N-methyl-N'-nitro-N-nitrosoguanidine) according to the conditions described in the literature (*J. Amer. Chem. Soc.* (1947), 69, 3028–3030).

In the case where D is an —SR$^{44}$ radical, the isothiourea derivatives of general formula (III.8) are prepared in 3 stages from the primary amine of general formula (III.2). The reaction of the benzoylisothiocyanate on the amine of general formula (III.2) in a solvent such as, for example, acetone, leads to the benzoyl-thiourea intermediates which are then hydrolysed in a standard fashion by heating in a basic medium. The thioureas thus obtained are then alkylated by a halogenated derivative R$^{44}$-Hal, by heating in an inert solvent, in order to produce the isothioureas of general formula (III.8).

The deprotection of the acid function of the intermediates of general formula (III.8) is then carried out in a standard fashion according to the nature of Gp$_2$, for example, by saponification using LiOH or according to methods described in the literature (T. W. Greene and P. G. M. Wuts, Protective Groups in Organic Synthesis, Second edition (Wiley-Interscience, 1991)).

Preparation of the Intermediates of General Formula (IV)

A) When A' is as defined above, W=—NR$^{45}$— and Y=—(CH$_2$)$_t$—(t=0), the amines of general formula (IV) are prepared according to the following synthesis strategies:

The non-commercial anilines of general formula (IV), derivatives of indoline or of 1,2,3,4-tetrahydroquinoline, Diagram 2.1, in which T and R$^{28}$ are as defined above, can be prepared from the corresponding nitro derivatives of general formula (IV.1). 6-nitro-1,2,3,4-tetrahydroquinoline is described in *Can. J. Chem.* (1952), 30, 720–722. Alkylation of the amine is carried out in a standard fashion by a strong base such as, for example, NaH, in a polar aprotic solvent such as, for example, DMF in the presence of a halogenated derivative R$^{28}$-Hal, such as for example, 3-dimethylaminopropane chloride or benzyl bromide. The nitro derivative of general formula (IV.2) obtained intermediately is then reduced, for example, by Raney nickel in the presence of hydrazine hydrate in order to produce anilines of general formula (IV).

Diagram 2.1

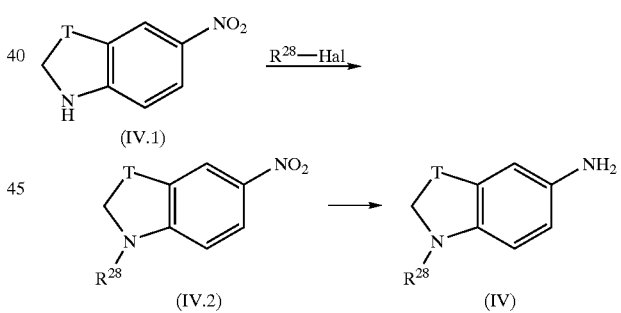

In the particular case of phenolic derivatives, the anilines of general formula (IV) are obtained by hydrogenation, in the presence of Pd/C, from the precursor nitrophenol derivatives. The nitrated derivatives of the di-alkylphenols are accessible according to a method described in *J. Org. Chem.* (1968) 33 (1), 223–226.

The intermediates of general formula (IV) in which A' is a diphenylamine are accessible by the methods described in the literature (*Synthesis* (1990) 430; *Indian J. Chem.* (1981) 20B, 611–613; *J. Med. Chem.* (1975) 18(4), 386–391) which involve the reduction of a nitrodiphenylamine intermediate. Reduction of the nitro function is carried out in a standard fashion by hydrogenation in the presence of a catalytic quantity of Pd/C in order to access the aminodiphenylamines of general formula (IV).

When A' is a carbazole derivative (Ω then represents a direct bond), the methods for preparation of the aminocarbazoles of general formula (IV) involve the synthesis of a nitrocarbazole intermediate. These methods are described in *Pharmazie* (1993) 48(11), 817–820; *Synth. Commun.* (1994) 24(1), 1–10; *J. Org. Chem.* (1980) 45, 1493–1496; *J. Org. Chem.* (1964) 29(8), 2474–2476; *Org. Prep. Proced. Int.* (1981) 13(6), 419–421 or *J. Org. Chem.* (1963) 28, 884. Reduction of the nitro function of the nitrocarbazole intermediates is, in this case, preferably carried out using hydrazine hydrate in the presence of Raney nickel.

The intermediates of general formula (IV) in which A' is a phenothiazine derivative (Ω represents a sulphur atom), are accessible using the methods of the literature which involve the synthesis of a nitrophenothiazine derivative. In particular, 3-nitrophenothiazine is described in *J. Org. Chem.* (1972) 37, 2691. Reduction of the nitro function in order to access the aminophenothiazines of general formula (IV) is carried out in a standard fashion by hydrogenation in the presence of a catalytic quantity of Pd/C in a solvent such as ethanol.

B) Alternatively, when $Y=-(CH_2)_q-O-$ and $W=-NR^{45}-$, the amines of general formula (IV), Diagram 2.2 (in which Alk represents an alkyl radical), can be prepared from the hydroquinones of general formula (IV.3) obtained according to the literature (*J. Chem. Soc. Perkin* 1 (1981) 303–306). Condensation on the commercial halogen esters of general formula (IV.4) is carried out in the presence of a base such as, for example $K_2CO_3$, while heating in a polar solvent such as, for example, THF for at least 5 hours. The esters of general formula (IV.5) obtained intermediately are then deprotected (in an acid medium in the case of the tert-butyl esters) in order to produce the acids of general formula (IV.6). The primary carboxamides of general formula (IV.7) are prepared using a concentrated aqueous solution of ammonium hydroxide, of DCC and HOBT in a solvent such as DMF. The reduction stage is carried out in an anhydrous medium, by heating to 70–80° C., in the presence of a selective reagent of carboxamides such as, for example, $BH_3$.THF, in a solvent such as, for example, THF in order to produce the amines of general formula (IV).

Diagram 2.2

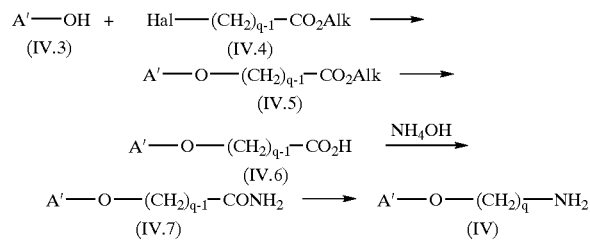

C) Moreover, when $Y=-(CH_2)_t-$ (with $t \neq 0$) and $W=-NR^{45}-$, the amines of general formula (IV), Diagram 2.3, are also accessible, for example, in two stages from the carboxylic acids of general formula (IV.8) according to a strategy similar to that described in Diagram 2.2 for intermediate (IV.6). The syntheses of the non-commercial carboxylic acids of general formula (IV.8) are described in the section on Preparation of the intermediates of general formula (IX).

Diagram 2.3

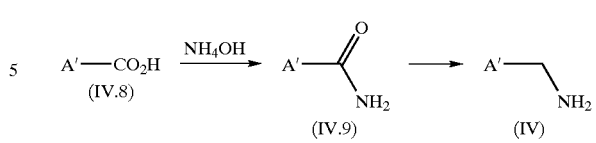

Preparation of the Intermediates of General Formula (VI)

A) When A is as defined above and $X=-(CH_2)_n-$ or $X=-CH=CH-(CH_2)_p-$ with n=1 or p=1, the aldehydes of general formula (VI) can be prepared from the nitriles or the corresponding carboxylic esters during a reduction stage in the presence, for example, of DIBAL or of another boron derivative, in an anhydrous solvent such as, for example, THF or dichloromethane, at a temperature varying from –78° C. to 20° C. Certain aldehydes are also accessible using methods described in the literature: *Bull. Chem. Soc. Jpn.* (1978) 51 (8), 2433–2434, *Bioorg. Med. Chem. Lett.* (1998) 8, 3453–3458.

B) Alternatively, when A is as defined above and $X=-O-(CH_2)_p-$, the aldehydes of general formula (VI), Diagram 3.1 (in which Alk represents an alkyl radical), can be prepared from the hydroquinones of general formula (VI.1) obtained according to the literature (*J. Chem. Soc. Perkin* 1 (1981) 303–306). Condensation with commercial halogen esters of general formula (VI.2) is carried out under the conditions previously described (Diagram 2.2) as well as the reduction of the ester to an aldehyde (paragraph A).

Diagram 3.1

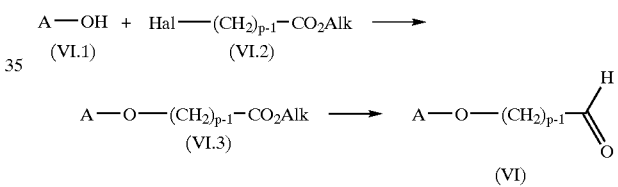

Preparation of the Intermediates of General Formula (VII)

The compounds of general formula (VII), Diagram 4.1, can be prepared from the intermediates of general formula (III.8), described in Diagram 1.1, where D, V and $R^1$ are as defined above, $Gp_1$ being a protective group of carbamate type and $Gp_2$ is an alkyl or arylalkyl group. Deprotection of the amine function is carried out in a standard fashion depending on the nature of $Gp_1$, for example, using a strong acid, such as for example 4N HCl in dioxane, or according to methods described in the literature (T. W. Greene and P. G. M. Wuts, Protective Groups in Organic Synthesis, Second edition (Wiley-Interscience, 1991)).

Diagram 4.1

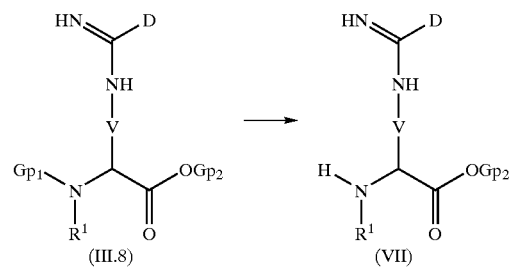

Preparation of the Intermediates of General Formula (IX)

The non-commercial acids of general formula (IX) are accessible using the methods in the literature. For example, trisnorlipoic acid [2-(1,2-dithiolan-3-yl) acetic acid] is obtained in 5 stages according to an experimental protocol described in *Tetrahedron Letters*. (1997), 38 (33), 5785–5788. The syntheses of the acids derived from phenothiazine are in particular described in *J. Med. Chem.* (1998), 41(2), 148–156 or *Bull. Soc. Chim. Fr.* (1960), 1049–1066.

Unless otherwise defined, all the technical and scientific terms used here have the same meanings as those generally understood by the ordinary specialist in the field to which this invention belongs. Similarly, all the publications, patent applications, all patents and all other references mentioned here are incorporated by way of reference.

The following examples are presented to illustrate the above procedures and must in no case be considered as a limit to the scope of the invention.

EXAMPLES

Example 1

(2S)-2-amino-N-(4-anilinophenyl)-5-{[imino(2-oxido-2-oxohydrazino)methyl]amino}pentanamide 1.1) tert-butyl (1S)-1-[(4-anilinoanilino)carbonyl]-4-{[imino(2-oxido-2-oxohydrazino)methyl]amino}butylcarbamate 1.03 g (5 mmol) of 1,3-dicyclohexylcarbodiimide is added to a solution of 1.6 g (5 mmol) of N-tert-butoxycarbonyl-L-nitroarginine and 0.92 g (5 mmol) of $N^1$-phenyl-1,4-benzediamine in 50 ml of DMF. The reaction mixture is agitated for 15 hours and finally concentrated under vacuum. The evaporation residue is taken up in 50 ml of AcOEt and filtered in order to eliminate the precipitate. The filtrate is then washed twice with 50 ml of a saturated solution of sodium carbonate and 50 ml of salt water. After drying over sodium sulphate, the organic solution is filtered and concentrated to dryness under vacuum. The residue obtained is purified on a silica column (eluent: heptane/AcOEt: 3/7 to 0/10). 0.8 g of a beige powder is obtained. Melting point: 93–94° C.

1.2) (2S)-2-amino-N-(4-anilinophenyl)-5-{[imino(2-oxido-2-oxohydrazino)methyl]-amino}pentanamide 2 ml (8 mmol) of a 4N solution of HCl in 1,4-dioxane is added to a solution of 0.4 g (0.8 mmol) of intermediate 1.1 in 10 ml of methanol, cooled down to 0° C. The reaction mixture is then agitated for 4 hours at 23° C. At the end of the reaction, the mixture is concentrated under vacuum in order to produce a beige powder which is purified by chromatography on a silica column (eluent $CH_2Cl_2$/MeOH: 9/1 to 8/2). The expected product is obtained in the form of a clear grey powder. Melting point: 68–72° C.

Example 2

(2S)-2-amino-5-{[imino(2-oxido-2-oxohydrazino)methyl]amino}-N-(1-methyl-2,3-dihydro-1H-indol-5-yl)pentanamide 2.1) 1-methyl-5-nitroindoline 25 ml of anhydrous DMF is introduced into a 150 ml three-necked flask, under an inert atmosphere, followed by 0.84 g (21 mmol) of 60% NaH. The reaction mixture is cooled down using an ice bath before the dropwise addition of a solution of 3.28 g (20 mmol) of 5-nitroindoline in 5 ml of anhydrous DMF. At the end of the addition, agitation is maintained for 1 hour at 23° C., before introducing dropwise a solution of 1.31 ml (21 mmol) of MeI in 5 ml of anhydrous DMF. Agitation is continued for 15 hours at 23° C. The reaction is finally neutralized, at 0° C., with 20 ml of a saturated solution of $NH_4Cl$. The reaction mixture is then diluted with 20 ml of water and 50 ml of AcOEt. After decanting, the organic phase is washed successively with 20 ml of water then 20 ml of salt water, dried over magnesium sulphate, filtered and concentrated under vacuum. A dark yellow powder is obtained.

2.2) 1-methyl-5-aminoindoline

Approximately 400 mg of Raney nickel is added to a mixture of 2.84 g (15.9 mmol) of 1-methyl-5-nitroindoline and 4 ml (80 mmol) of hydrazine hydrate in 60 ml of absolute ethanol. The reaction mixture is heated under reflux for 5 hours. After returning to 23° C., a little silica is added to the flask and the solvent is evaporated off under vacuum. The evaporation residue is placed directly at the top of a chromatography column. The expected product is eluted using a heptane/AcOEt mixture (3/7). A violet powder is obtained (65%) which is used directly in the following stage.

2.3) (2S)-2-amino-5-{[imino(2-oxido-2-oxohydrazino)methyl]amino}-N-(1-methyl-2,3-dihydro-1H-indol-5-yl)pentanamide The experimental protocol used is the same as that described for Example 1, intermediate 2.2 replacing the $N^1$-phenyl-1,4-benzenediamine. After purification on a silica column (eluent: $CH_2Cl_2$/EtOH: 10/1), an off-white solid is obtained. Melting point: 140–142° C.

Example 3

(2S)-2-[(3,5-ditert-butyl-4-hydroxybenzyl)amino]-5-{[imino(2-oxido-2-oxohydrazino)methyl]amino}pentanoic acid 3.1) methyl (2S)-2-[(3,5-ditert-butyl-4-hydroxybenzyl)amino]-5-{[imino(2-oxido-2-oxohydrazino)methyl]amino}pentanoate 1.17 g (5 mmol) of 3,5-ditert-butyl-4-hydroxybenzaldehyde, 1.35 g (5 mmol) of the methyl ester of L-nitroarginine are introduced successively into a three-necked flask, under an argon atmosphere, containing 3 g of pulverulent 3 Å molecular sieve, previously activated, in suspension in 50 ml of anhydrous MeOH, followed by 0.7 ml (5 mmol) of $Et_3N$. The reaction mixture is agitated for 15 hours, at 23° C., before the addition, at 0° C., of 0.35 g (5.5 mmol) of sodium cyanoborohydride. Agitation is maintained for another 4 hours at 23° C. The suspension is then filtered on a Büchner and the filtrate is diluted with 150 ml of AcOEt and 50 ml of water. After agitation and decanting, the organic phase is washed with 50 ml of salt water. The organic solution is then dried over sodium sulphate, filtered and concentrated to dryness under vacuum. The evaporation residue is then purified on a silica column (eluent: heptane/AcOEt 1/9). A clear salmon powder is obtained with a yield of 31%. Melting point: 55–56° C.

3.2) (2S)-2-[(3,5-ditert-butyl-4-hydroxybenzyl)amino]-5-{[imino(2-oxido-2-oxohydrazino)methyl]amino}pentanoic Acid A solution of 90 mg (2.1 mmol) of LiOH in 10 ml of water is added, at 0° C., to a solution of 0.45 g (1 mmol) of intermediate 3.1 in 10 ml of THF. The mixture is agitated for 1 hour to 23° C. before dilution with 25 ml of AcOEt. After agitation, the mixture is decanted and the basic,aqueous phase, is again washed with 25 ml of AcOEt. The basic solution is then neutralised, at 0° C., with 1N HCl. The precipitate which appears is then filtered and washed successively with 25 ml of water and 25 ml of AcOEt. After drying, a white powder is obtained with a yield of 35%. Melting point: 196–197° C.

Example 4
methyl (2S)-2-{[5-(1,2-dithiolan-3-yl)pentanoyl]amino}-5-{[imino(2oxido-2-oxido-2-oxohydrazino)methyl]amino}pentanoate 1.35 g (5 mmol) of L-nitroarginine methyl ester hydrochloride, triethylamine (2.1 ml), 0.676 g (5 mmol) of hydroxybenzotriazole and 0.956 g (5 mmol) of 1-(3-dimethylaminopropyl)-3-ethyl-carbodiimide hydrochloride are added successively to a solution of 1.03 g (5 mmol) of (DL)-thioctic acid in 50 ml of dichloromethane. After agitating the reaction mixture overnight at 25° C., the mixture is diluted with 400 ml of water and agitation is maintained for another 30 minutes. The product is extracted 3 times with 200 ml of dichloromethane. The organic solution is dried over magnesium sulphate, filtered and concentrated under vacuum. The solid obtained is purified by recrystallization from a mixture of isopropyl acetate and dichloromethane (80/20), filtered and rinsed with diethyl ether in order to obtain, after drying, 1.77 g of a yellow solid with a yield of 84%. Melting point: 96.6–97° C.

Example 5
(2S)-2-{[5-(1,2-dithiolan-3-yl)pentanoyl]amino}-5-{[imino(2-oxido-2-oxohydrazino)methyl]amino}pentanoic acid 2.3 ml of a solution (1M in $H_2O$) of lithium hydroxide is added dropwise to a solution of 0.632 g (1.50 mmol) of compound 4 in 10 ml of THF and agitation is maintained at ambient temperature for 1 hour. The pH is adjusted to 5–6 with HCl (1M) followed by extraction with diethyl ether. The organic solution is dried over magnesium sulphate, filtered and evaporated under reduced pressure. The solid obtained is purified by recrystallization from ethanol, filtered and rinsed with diethyl ether in order to obtain, after drying, 0.370 g of a pale yellow solid with a yield of 61%. Melting point: 140–143.1° C.

Pharmacological Study of the Products of the Invention

Study of the Effects on Neuronal Constitutive NO Synthase of a Rat' s Cerebellum The inhibitory activity of the products of the invention is determined by measuring their effects on the conversion by NO synthase of [$^3$H]L-arginine to [$^3$H]L-citrulline according to the modified method of Bredt and Snyder (*Proc. Natl. Acad. Sci. USA*, (1990) 87: 682–685). The cerebellums of Sprague-Dawley rats (300 g-Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 µl of incubation buffer containing 100 mM of HEPES (pH 7.4), 2 mM of EDTA, 2.5 mM of $CaCl_2$, 2 mM of dithiotreitol, 2 mM of reduced NADPH and 10 µg/ml of calmodulin are distributed. 25 µl of a solution containing 100 nM of [$^3$H]L-arginine (Specific activity: 56.4 Ci/mmole, Amersham) and 40 µM of non-radioactive L-arginine is added. The reaction is initiated by adding 50 µl of homogenate, the final volume being 200 µl (the missing 25 µl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer. The compound of Examples 1 and 2 described above shows an $IC_{50}$ lower than 10 µM.

Study of the Effects on the Oxidation Stress Induced by Glutamate on Cells in Culture (HT-22).

The inhibitory activity of the products of the invention is determined by measuring their ability to protect the cells of a mouse hippocampal line (HT-22) from an oxidation stress caused by glutamate. The biosynthesis of glutathione, an essential element of cell detoxification of free radicals, requires the active transport of cystine to the interior of the cell. The glutamate by opposing the penetration of cystine causes a reduction in the level of glutathione which leads to the death of the cell due to oxidation stress (Demerlé-Pallardy, C. et al., *J. Neurochem.* (2000) 74, 2079–2086; Murphy, T. H. et al., *Neuron*, (1989) 2: 1547–1558). The cells are cultured at 37° C. in a DMEM medium with 10% of foetal calf serum added to it. The tests are carried out in 96-well plates containing 5000 cells per well. The glutamate (5 mM) is added to the medium containing or not containing the products to be tested. The cell viability is tested after 24 h by the MTT method (Hansen, M. B. et al., *J Immunol. Methods* (1989), 119, 203–210). The ability of the compounds to protect the cells from the toxic action of the glutamate is estimated in $EC_{50}$, calculated relative to the viability of cells which have not been subjected to the action of glutamate considered as 100% viability. The compounds of Examples 1 and 2, described above show an $EC_{50}$, lower than 25 µM.

What is claimed is:

1. A compound of formula

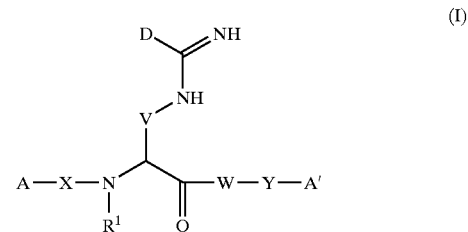

(I)

wherein $R^1$ is hydrogen or alkyl;
one of A and A' is

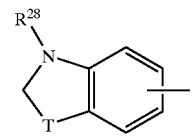

and the other is hydrogen,
$R^{28}$ is selected from the group consisting of hydrogen, alkyl, aminoalkyl, alkylaminoalkyl, dialkylaminoalkyl and aralkyl with the aryl unsubstituted or substituted by at least one, member selected from the group consisting of —OH, halogen, alkyl, alkoxy, nitro and
—$NR^{29}R^{30}$, $R^{29}$ and $R^{30}$ are individually selected from the group consisting of hydrogen, alkyl, and —$COR^{31}$ or $R^{29}$ and $R^{30}$ together with the nitrogen form an unsubstituted or substituted heterocycle of 4 to 7 ring members and 1 to 3 heteroatoms selected from the group consisting of N, O and S, $R^{31}$ is selected from the group consisting of hydrogen, alkyl, alkoxy, and —$NR^{32}R^{33}$,
$R^{32}$ and $R^{33}$ are individually hydrogen or alkyl or $R^{32}$ and $R^{33}$ together with the nitrogen atom form an unsubstituted or substituted heterocycle of 4 to 7 ring members and 1 to 3 herteroatoms selected from the group consisting of O, N and S,
T is —$(CH_2)_m$ with m=1 or 2;
D is selected from the group consisting of alkyl of 1 to 6 carbon atoms, carbocyclic or heterocyclic aryl with 5 or 6 ring members containing 1 to 4 heteroatoms selected from the group consisting of O, S and N, the carbocyclic or heterocyclic aryl unsubstituted or substituted by at least one member selected from the group consisting of alkyl, alkenyl and alkoxy of up to 6 carbon atoms, or D is —NR$^{42}$R$^{43}$, R$^{42}$ and R$^{43}$ are individually selected from the group consisting of hydrogen, alkyl, alkenyl and alkynyl to 6 carbon atoms, cyano, nitro and amino, or R$^{42}$ and R$^{43}$ together with the nitrogen form a non-aromatic heterocycle of five to six ring members, the elements of the chain being selected from the group consisting of —CH$_2$—, —NH—, —O— and —S—;

or D is —SR$^{44}$, R$^{44}$ is alkyl of 1 to 6 carbon atoms unsubstituted or substitute with a member selected from the group consisting of —OH, halogen, amino, cyano and aralkyl; X is selected from the group consisting of —(CH$_2$)$_n$—, —(CH$_2$)$_n$—CO—, —O—(CH$_2$)$_p$——S—(CH$_2$)$_p$, —CH=CH—(CH$_2$)$_p$— and —CH=CH—(CH$_2$)$_n$—CO—, n is an integer from 0 to 6 and p is an integer from 1 to 6;

W is —O— or —NR$^{45}$,

R$^{45}$ is hydrogen or alkyl;

Y is selected from the group consisting of —(CH$_2$)$_t$—, —(CH$_2$)$_q$—O—, —(CH$_2$)$_q$—S— and —(CH$_2$)$_q$—NR$^{46}$—, R$^{46}$ is hydrogen or alkyl, t is an integer from 2 to 6;

and q is an integer from 2 to 6;

V is selected from the group consisting of —(CH$_2$)$_r$, —(CH$_2$)$_r$—O—(CH$_2$)$_s$—, —(CH$_2$)$_r$—S—(CH$_2$)$_s$—, —(CH$_2$)$_r$—S—(O)—(CH$_2$)$_s$— and —(CH$_2$)$_r$—S(O)$_2$—(CH$_2$)$_s$— r is an integer from 1 to 6;

s is an integer from 2 to 6;

and a pharmaceutically acceptable salt thereof.

2. A compound of claim 1, wherein:

D is carbocyclic or heterocyclic aryl with 5 or 6 ring members containing 1 to 4 heteroatoms selected from the group consisting of O, S and N, the carbocyclic or heterocyclic aryl being unsubstituted or substituted by at least one member selected from the group consisting of alkyl, alkenyl and alkoxy of up to 6 carbon atoms, or D is —NR$^{42}$R$^{43}$, R$^{42}$ and R$^{43}$ are individually selected from the group consisting of hydrogen, alkyl, alkenyl and alkynyl of up to 6 carbon atoms, cyano, nitro and amino, or R$^{42}$ and R$^{43}$ together with the nitrogen form a non-aromatic heterocycle with five to six ring members, the elements of the chain being selected from the group consisting of —CH$_2$—, —NH——O— and —S—;

V is selected from the group consisting of —(CH$_2$)$_r$—, —(CH$_2$)$_r$—O—(CH$_2$)$_s$ and —(CH$_2$)$_r$—S—(CH$_2$)$_s$—, r is an integer from 1 to 6 and s is an integer from 2 to 6;

W is —O—or —NH

X is selected from the group consisting of —(CH$_2$)$_n$—, —(CH$_2$)$_n$—CO—, —O—(CH$_2$)$_p$— and —S—(CH$_2$)$_p$, n is an integer from 0 to 6 and p is an integer from 1 to 6;

Y is selected from the group consisting of —(CH$_2$)$_t$—, —(CH$_2$)$_q$—O— and —(CH$_2$)$_q$—NR$^{46}$—, R$^{46}$ is hydrogen or alkyl, t is an integer from 0 to 6 and q is an integer from 2 to 6.

3. A compound of claim 1 wherein X is —(CH$_2$)$_n$— and n is an integer from 0 to 6.

4. A compound of claim 1 wherein V is —(CH$_2$)$_r$— and r is an integer from 1 to 6.

5. A compound of claim 1 wherein W is —NH—, Y is —(CH$_2$)$_t$— and t is an integer from 0 to 6.

6. A compound of claim 1 wherein D is —NHNO$_2$.

7. A compound of claim 1 wherein R$^{28}$ is alkyl.

8. A compound of claim 7 wherein R$^{28}$ is methyl.

9. A compound of claim 1 which is (2S)-2-amino-5-{[imino(2-oxido-2-oxohydrazino)methyl]amino}-N-(1-methyl-2,3-dihydro-1H-Indol-5-yl)pentanamide, or a pharmaceutically acceptable salt thereof.

10. A pharmaceutical composition comprising, as active ingredient, a compound of claim 1 or a pharmaceutically acceptable salt thereof, and a pharmaceutical carrier.

11. A pharmaceutical composition of claim 10 wherein the compound of claim 1 or its pharmaceutically acceptable salt is (2S)-2-amino-5-{imino(2-oxido-2-oxohydrazino)methyl]amino}-N-(1-methyl-2,3-dihydro-1H-indol-5-yl)pentanamide, or a pharmaceutically acceptable salt thereof.

* * * * *